(12) United States Patent
Cohen et al.

(10) Patent No.: US 7,922,658 B2
(45) Date of Patent: Apr. 12, 2011

(54) SURGICAL RETRACTOR DEVICE AND RELATED METHODS

(75) Inventors: Dan S. Cohen, Miami Beach, FL (US); Nicholas J. Bender, Lake Hiawatha, NJ (US); Oliver Buchert, Franklin Lakes, NJ (US); Rui J. Ferreira, Livingston, NJ (US)

(73) Assignee: EBI, LLC, Parsippany, NJ (US)

( * ) Notice: Subject to any disclaimer, the term of this patent is extended or adjusted under 35 U.S.C. 154(b) by 19 days.

(21) Appl. No.: 12/256,106

(22) Filed: Oct. 22, 2008

(65) Prior Publication Data
US 2009/0203969 A1 Aug. 13, 2009

Related U.S. Application Data

(63) Continuation-in-part of application No. 11/558,095, filed on Nov. 9, 2006.

(60) Provisional application No. 60/981,673, filed on Oct. 22, 2007.

(51) Int. Cl.
*A61B 1/32* (2006.01)

(52) U.S. Cl. ........................ 600/223; 600/210

(58) Field of Classification Search ........... 600/201–246
See application file for complete search history.

(56) References Cited

U.S. PATENT DOCUMENTS

| 4,344,419 A * | 8/1982 | Burgin ...................... 600/212 |
| 4,610,243 A | 9/1986 | Ray |
| 4,926,849 A | 5/1990 | Downey |
| 5,351,680 A | 10/1994 | Jung |
| 5,512,038 A | 4/1996 | O'Neal et al. |
| 5,616,117 A | 4/1997 | Dinkler et al. |
| 5,728,046 A | 3/1998 | Mayer et al. |
| 5,795,291 A | 8/1998 | Koros et al. |
| 5,813,978 A | 9/1998 | Jako |
| 5,828,139 A | 10/1998 | Slater |
| 5,882,298 A | 3/1999 | Sharratt |
| 5,908,382 A | 6/1999 | Koros et al. |
| 5,944,658 A | 8/1999 | Koros et al. |
| D415,274 S | 10/1999 | Koros et al. |
| 5,993,385 A | 11/1999 | Johnston et al. |
| D442,687 S | 5/2001 | Schulz |
| 6,224,545 B1 | 5/2001 | Cocchia et al. |

(Continued)

FOREIGN PATENT DOCUMENTS

DE 20119971 3/2002

(Continued)

OTHER PUBLICATIONS

PCT Invitation To Pay Additional Fees, date of mailing May 13, 2008, with a partial International Search Report, for PCT/US2007/023708.

(Continued)

*Primary Examiner* — Eduardo C Robert
*Assistant Examiner* — Christina Negrelli
(74) *Attorney, Agent, or Firm* — Harness, Dickey

(57) ABSTRACT

A blade for a surgical retractor. The blade includes a base portion and a distal portion. The base portion may be attached to a frame of a surgical retractor. The distal portion may be removably coupled to the base portion and may be unitarily constructed of a translucent material. A light source may be removably coupled to the distal portion. The distal portion may be disposable.

16 Claims, 20 Drawing Sheets

U.S. PATENT DOCUMENTS

| | | | |
|---|---|---|---|
| 6,416,467 B1 | 7/2002 | McMillin et al. | |
| D475,975 S | 6/2003 | Fox | |
| 6,616,605 B2 | 9/2003 | Wright et al. | |
| 6,712,795 B1 | 3/2004 | Cohen | |
| 6,869,398 B2 | 3/2005 | Obenchain et al. | |
| 6,945,933 B2 | 9/2005 | Branch et al. | |
| D568,471 S | 5/2008 | Engler | |
| D575,396 S | 8/2008 | Wu | |
| D589,145 S | 3/2009 | Miller | |
| 2004/0176665 A1 | 9/2004 | Branch et al. | |
| 2004/0215199 A1 | 10/2004 | Zinkel | |
| 2005/0192485 A1 | 9/2005 | Branch et al. | |
| 2005/0277812 A1 | 12/2005 | Myles | |
| 2006/0052672 A1 | 3/2006 | Landry et al. | |
| 2007/0073111 A1 | 3/2007 | Bass | |
| 2007/0100212 A1 | 5/2007 | Pimenta et al. | |
| 2007/0293729 A1* | 12/2007 | Grey et al. | 600/212 |
| 2008/0033251 A1* | 2/2008 | Araghi | 600/235 |
| 2008/0183046 A1 | 7/2008 | Boucher et al. | |
| 2009/0018399 A1 | 1/2009 | Martinelli et al. | |

FOREIGN PATENT DOCUMENTS

| | | |
|---|---|---|
| EP | 143124 A1 | 6/1985 |
| EP | 1435219 | 7/2004 |
| WO | WO-2005016131 A2 | 2/2005 |
| WO | WO-2006042241 A2 | 4/2006 |

OTHER PUBLICATIONS

PCT International Preliminary Report on Patentability, date of mailing May 22, 2009, Written Opinion of the International Searching Authority for PCT/US2007/023708.

Partial European Search Report, date of mailing Jan. 18, 2010, for EP 09013262.2-1269.

Office Action mailed Dec. 29, 2008 in pending U.S. Appl. No. 11/558,095, filed Nov. 9, 2006.

Office Action mailed Jun. 3, 2009 in pending U.S. Appl. No. 11/558,095, filed Nov. 9, 2006.

Advisory Action mailed Aug. 20, 2009 in pending U.S. Appl. No. 11/558,095, filed Nov. 9, 2006.

* cited by examiner

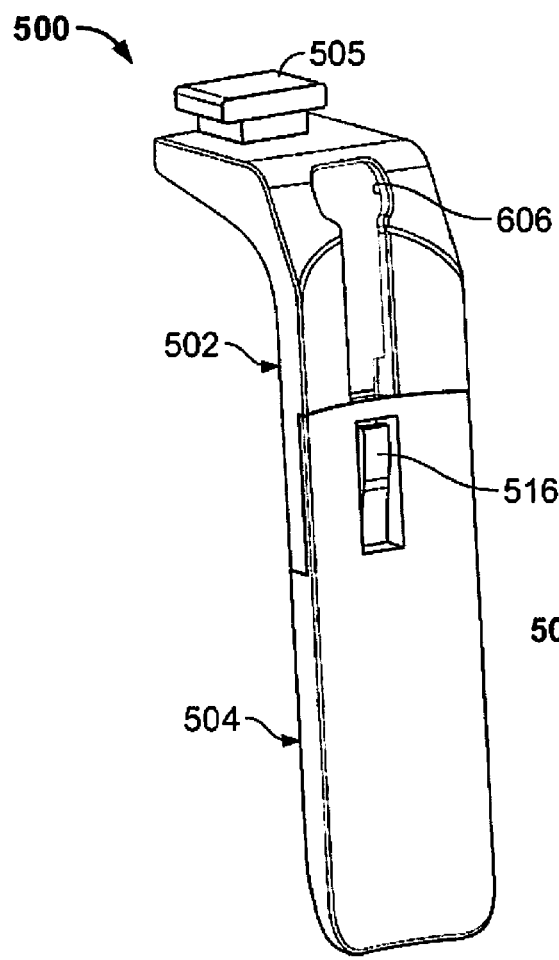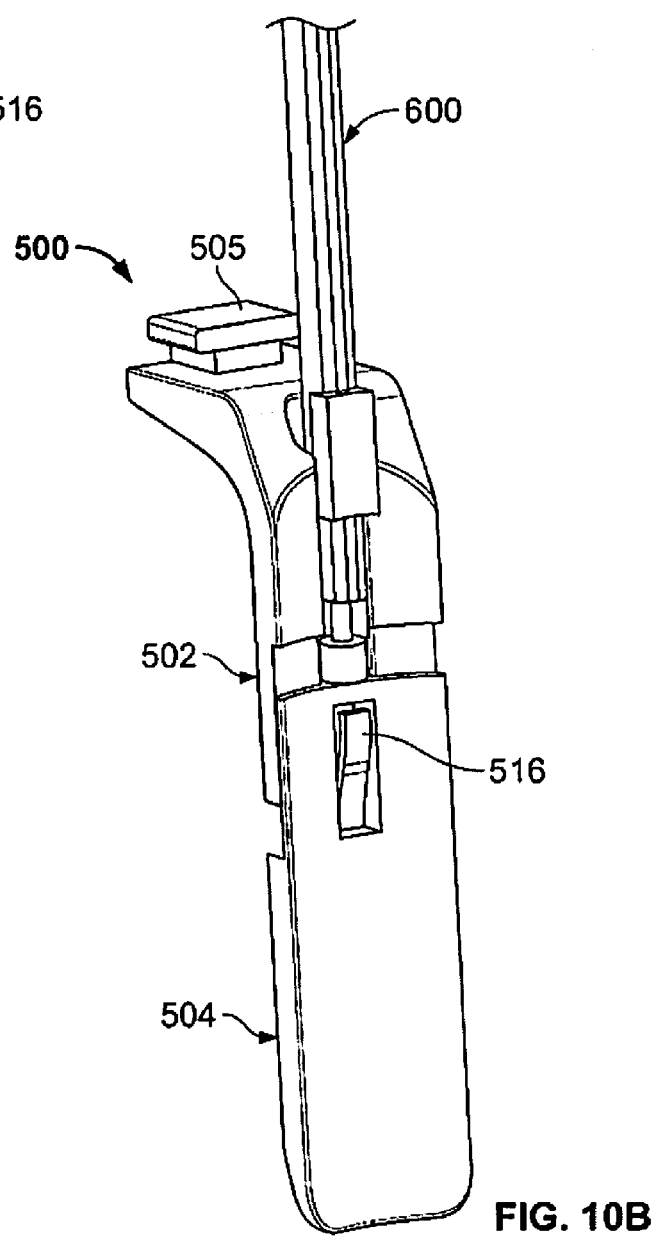
FIG. 10A
FIG. 10B

SURGICAL RETRACTOR DEVICE AND RELATED METHODS

CROSS-REFERENCE TO RELATED APPLICATIONS

This application is a continuation-in-part of U.S. patent application Ser. No. 11/558,095 filed on Nov. 9, 2006. This application claims the benefit of U.S. Provisional Application No. 60/981,673, filed on Oct. 22, 2007. The entire disclosures of each of the above applications are incorporated herein by reference.

Various devices and associated methods are known for providing surgical access to portions of the human body. Such devices include, for example, forceps, dilators and retractors.

Continuing concern with reducing trauma, infection risk, and patient recovery time, encourages the development of instruments that may help reduce the invasiveness of surgical procedures. The present teachings provide such a surgical retractor device and associated methods for providing access to portions of the body.

SUMMARY

The present teachings provide a surgical retractor device. The surgical retractor device includes a frame having an outer frame member and an inner frame member coupled to the outer frame member for relative movement about a frame pivot axis, and a frame driver operable to rotate the outer frame member relative to the inner frame member about the frame pivot axis.

The present teachings also provide a surgical retractor device including a frame, a modular arm, and an arm connector releasably and self-lockingly coupling the modular arm to the frame, the arm connector allowing rotational motion of the modular arm relative to an axis of the frame.

The present teachings further provide a surgical retractor device for retracting a surgical opening of a patient. The surgical retractor device includes a generally U-shaped first frame member, the U-shaped first frame member defined by first and second end portions interconnected by an intermediate portion, a first quick engagement formation defined by the first end portion, at least one retractor arm coupled to the intermediate portion and movable in translation relative to the intermediate portion, and a modular arm coupled to the first quick engagement formation, the first modular arm rotatable relative to the first end portion.

The present teachings further provide a method of retracting a surgical opening of a patient. The method includes positioning a retractor having a frame relative to the surgical opening, pivoting a first frame member relative to a second frame member about a frame pivot axis, and inserting first and second retractor blades coupled to the frame into the surgical opening.

The present teachings still further provide a blade for a surgical retractor. The blade includes a base portion and a distal portion. The base portion may be attached to a frame of a surgical retractor. The distal portion may be removably coupled to the base portion and may be unitarily constructed of a translucent material. A light source may be removably coupled to the distal portion. The distal portion may be disposable.

Further areas of applicability of the present invention will become apparent from the description provided hereinafter. It should be understood that the description and specific examples are intended for purposes of illustration only and are not intended to limit the scope of the invention.

BRIEF DESCRIPTION OF THE DRAWINGS

The present invention will become more fully understood from the detailed description and the accompanying drawings, wherein:

FIGS. 10A-10D are a series of perspective views of a blade assembly according to the present teachings, a distal tip of the blade assembly is shown in various predetermined positions relative to a base of the blade assembly, FIG. 10B shown operatively associated with an extension instrument and FIGS. 10C and 10D shown operatively associated with a retraction instrument;

DESCRIPTION OF VARIOUS ASPECTS

The following description is merely exemplary in nature and is in no way intended to limit the invention, its application, or uses. The present teachings can be used for various surgical procedures in which access to portions of the body is desired, such as, for example, various orthopedic procedures, including anterior, posterior, or lateral spine surgeries. Furthermore, the present teachings can be used for retracting soft tissue, such as retracting open a small incision, and generally for maneuvering and aligning various implants and instruments through a limited area, such as, for example, in minimally invasive procedures.

Figure 1:
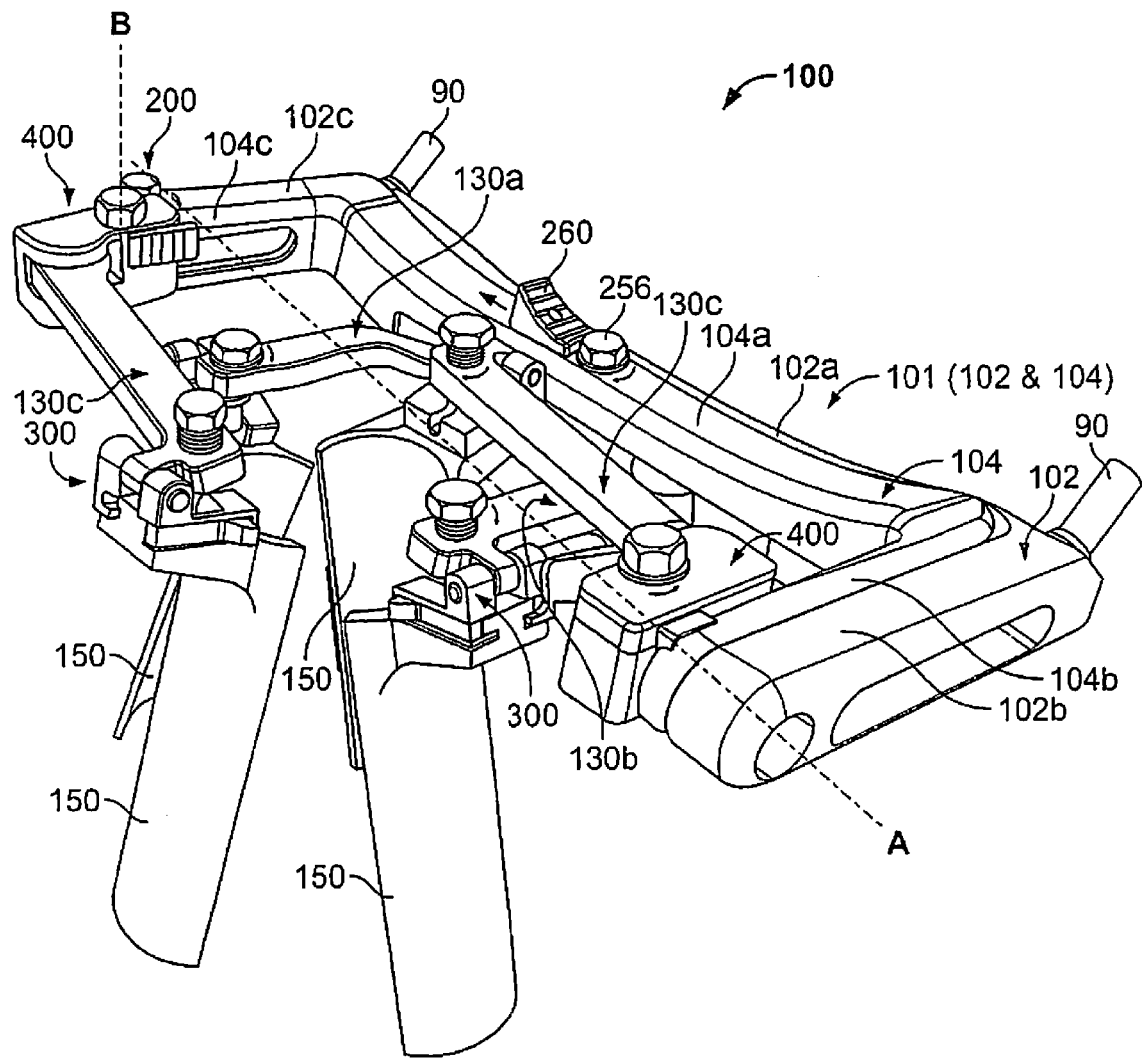
FIG. 1 is a perspective view of an exemplary retractor device according to the present teachings.
Figure 2:
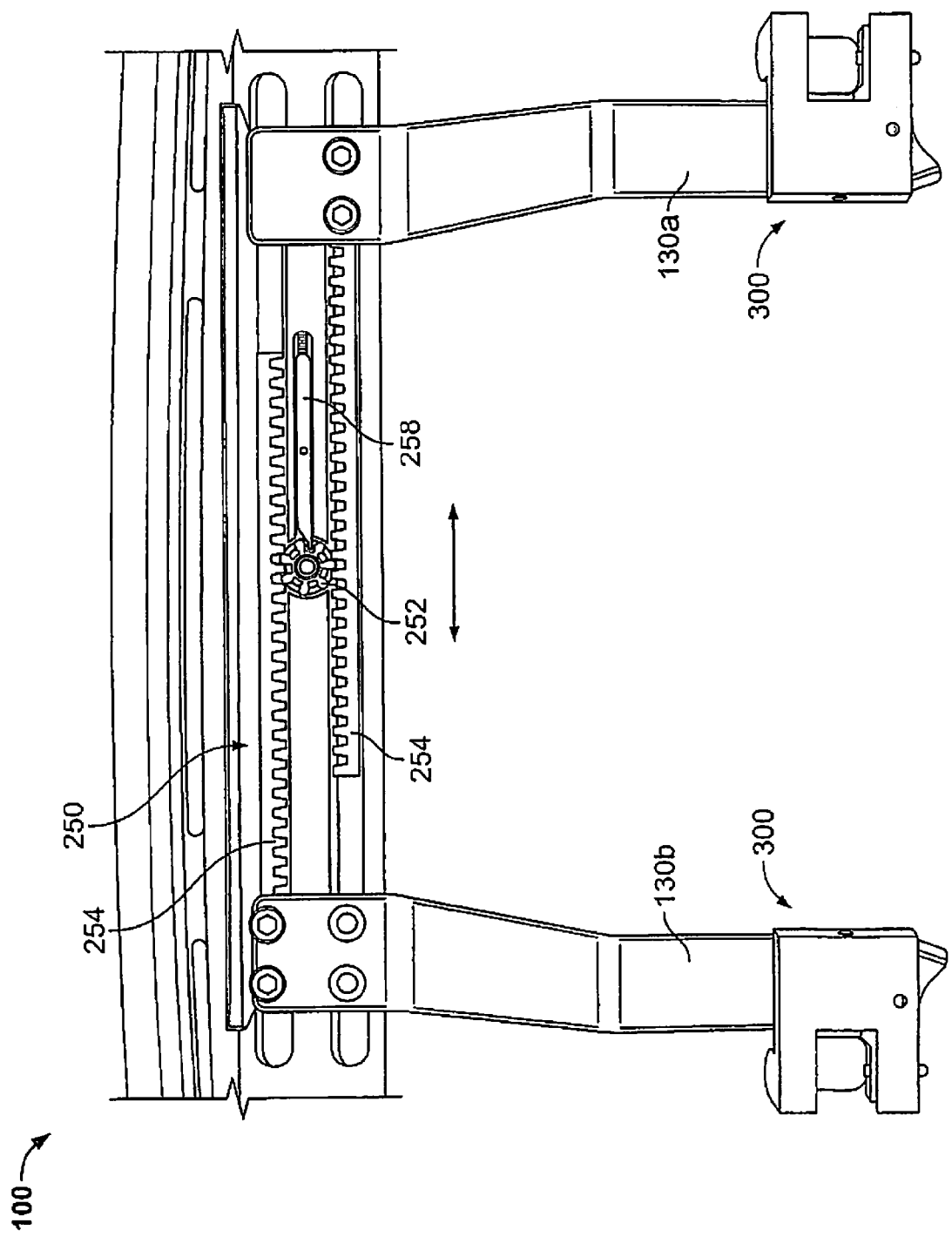
FIG. 2 is a partial bottom view of an exemplary retractor device according to the present teachings shown with a partial cut-away view of an distraction driver.

Referring to FIG. 1, an exemplary surgical retractor device according to the present teachings is illustrated and generally identified at reference character 100. The retractor device 100 can be shaped to fit the contour of the human body and as such the retractor device 100 can be flat, concave, convex, faceted, or any combination thereof. The retractor device 100 can include a frame 101 comprising an outer frame member 102, and an inner frame member 104 coupled to the outer frame member 102 by pivot pins or other linking elements 106, for pivotable motion about a frame pivot axis A. The outer frame member 102 can include a center or intermediate portion 102a and first and second end portions 102b, 102c arranged to generally define a U-like shape. Similarly, the inner frame member 104 can include an intermediate portion 104a and first and second end portions 104b, 104c arranged to generally define a U-like shape. The frame 101 can also include mounting stems 90 for connecting the frame 101 with a surgical table or other surgical structure in a known manner. The intermediate portions 102a, 104a of the frame 101 can have a convex or otherwise shaped lower surface for following the contour of the patient's anatomy. The frame 101 can also include various slots or windows for reducing weight, improving visualization and manipulation of the frame and related tools.

The outer and inner frame members 102, 104 can be pivotably coupled at the distal ends of their respective first end portions 102b, 104b and second end portions 102c, 104c in a nested-like configuration such that their respective intermediate portions 102a, 104a are adjacent to each other, and similarly, their respective first end portions 102b, 104b, and their respective second end portions 102c, 104c, are also adjacent to each other. The nested-like arrangement of the outer and inner frame members 102, 104 and their U-like shapes can provide free space for instrumentation and can reduce occlusion.

Figure 3A:
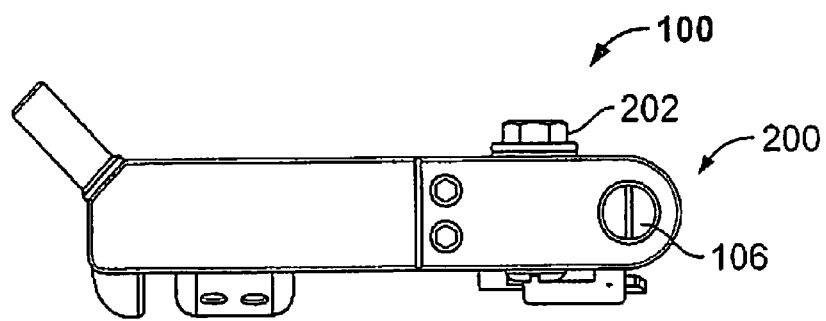
FIGS. 3A-3C are side views of an exemplary retractor device according to the present teachings with first and second frames shown in three different configurations.
Figure 3B:
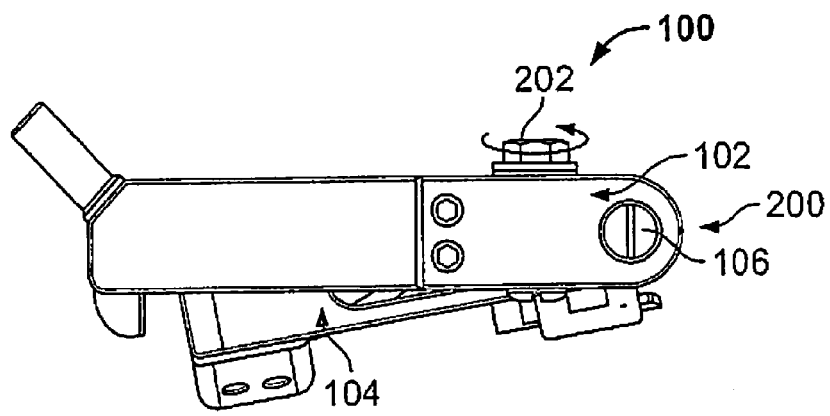
Figure 3C:
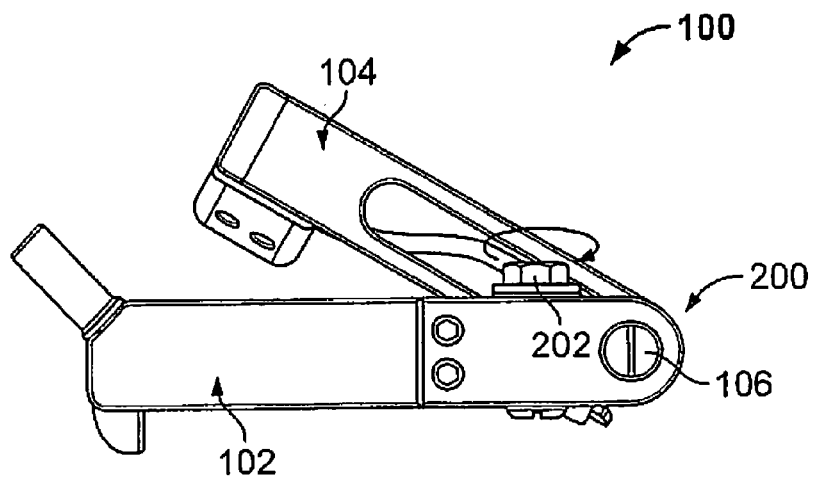
Figure 5:
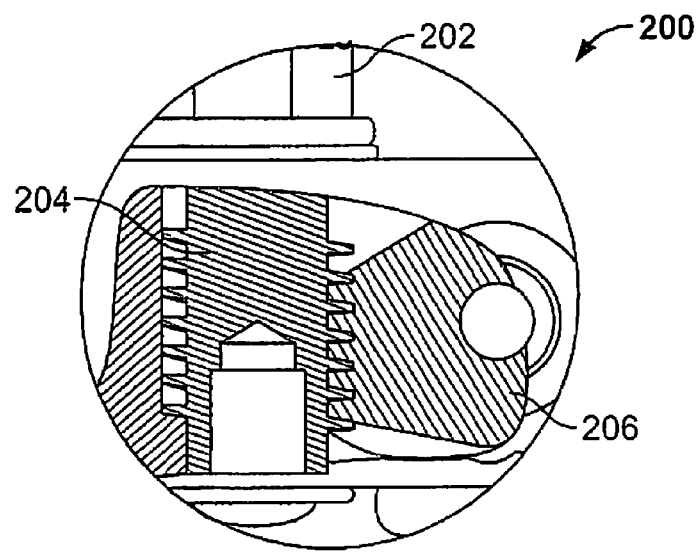
FIG. 5 is an enlarged sectional view of Detail A of FIG. 4.

Referring to FIG. 3A, the outer and inner frame members 102, 104 are shown in a neutral position in which the outer and inner frame members 102, 104 are substantially coplanar. A frame driver 200, shown in FIG. 5, can be actuated using a frame actuator 202. Rotating the actuator 202 in opposite directions can cause the inner frame member 104 to angle downward or upward relative to the outer frame member 102 in a continuous, non-incremental motion, as shown in FIGS. 3B and 3C. The frame driver 200 can be a gear-type driver, including, for example, a worm drive 204, and a gear 206 engaged to the worm drive 204 and connected to the linking element 106. Rotating the actuator 202 causes the worm drive 204 to rotate, driving the gear 206 and pivoting the inner frame member 104 relative to the outer frame member 102. The outer and inner frame members 102, 104 are held in the relative position reached when rotation of the actuator 202 ceases through the teeth meshing of the worm drive 204 and the gear 206.

Figure 7:
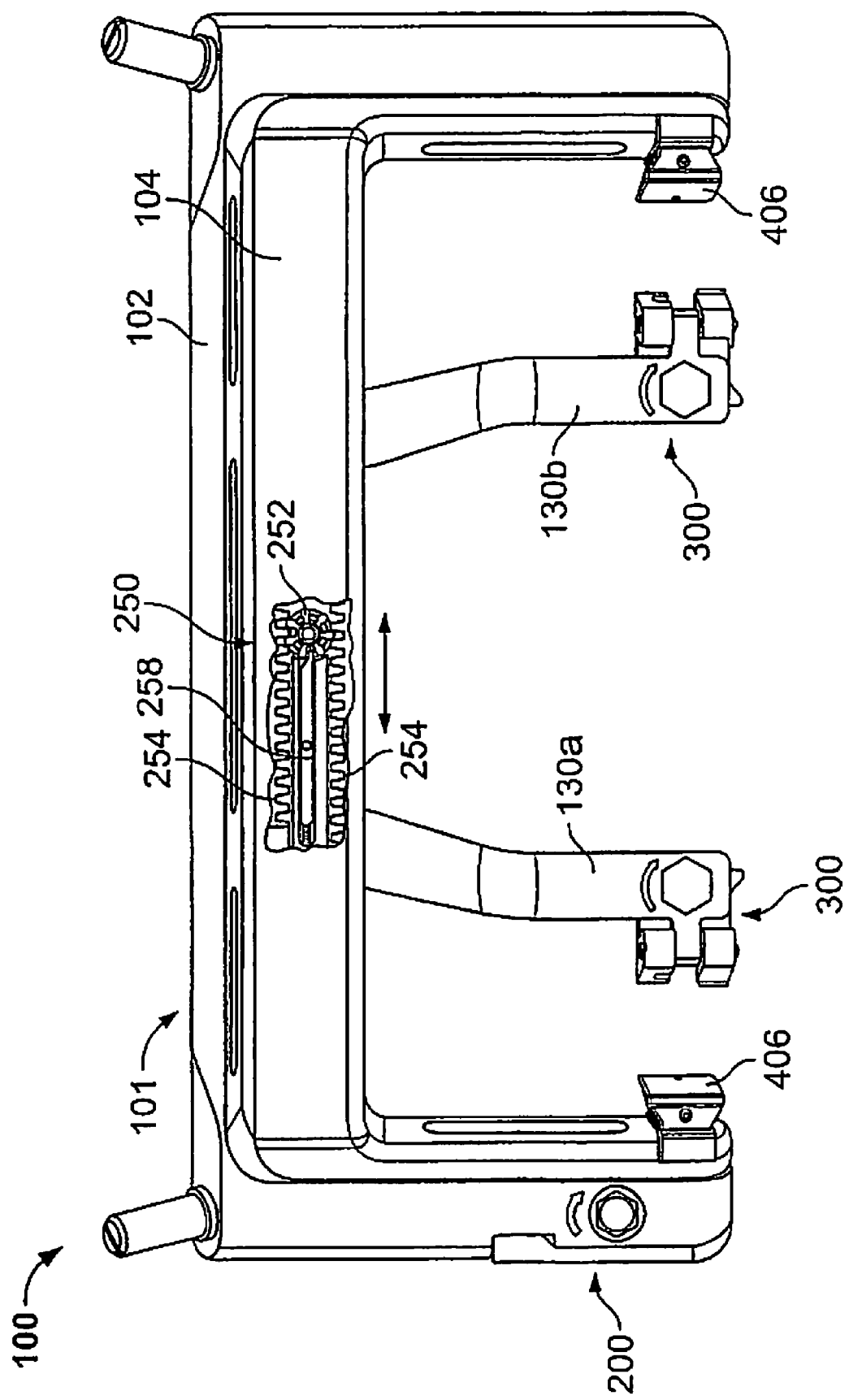
FIG. 7 a perspective top view of FIG. 4 shown with a partial cut-away view of a frame.

Referring to FIGS. 1, 2, 4, and 7, the retractor device 100 can include first and second retractor arms 130a, 130b movably connected at their proximal ends to the intermediate portion 104a of the inner frame member 104. A distraction or linear driver 250 can be used to drive the first and second retractor arms 130a, 130b closer together or further apart for distraction in a linear/translational motion, as shown in FIG. 7. The distraction driver 250 can include a pinion 252 that engages geared racks 254 coupled to the retractor arms 130a, 130b. Rotating the pinion 252 with a distraction actuator 256 drives the racks 254 to move the retractor arms 130a, 130b relative to one another. The first and second retractor arms 130a, 130b can move, for example, simultaneously from a center position outwardly away from each other, and inwardly toward each other. The actuator 256 can be, for example, a hex head attached to the pinion 252. A biased stopper 258 can be used to prevent motion of the first and second retractor arms 130a, 130b. The stopper 258 can be moved to a release position against bias by a moving a release element 260 connected to the stopper 258. In other applications, it may be desirable to only move one of the retractor arms 130a or 130b relative to the frame 101.

Figure 4:
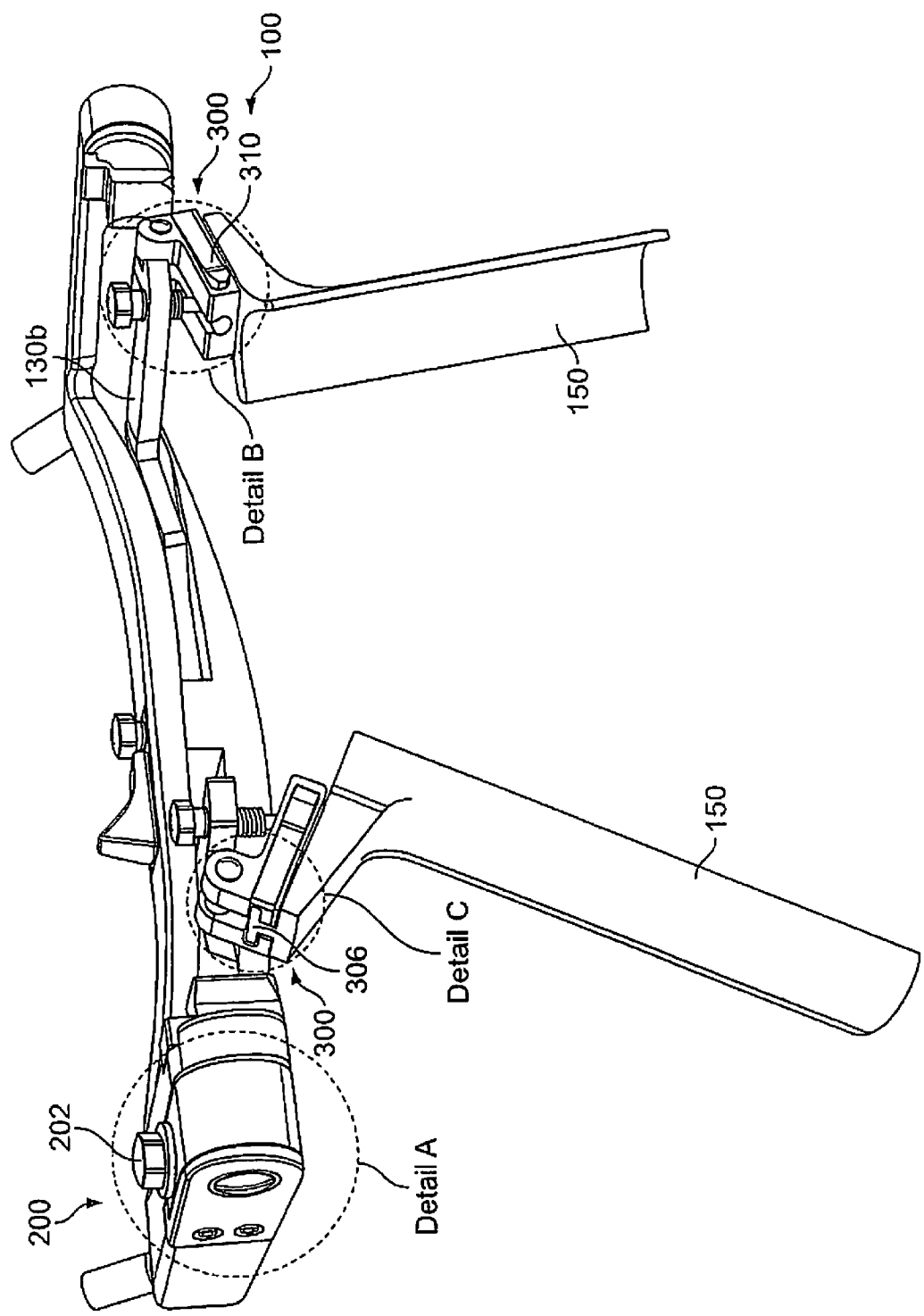
FIG. 4 is a perspective view of an exemplary retractor device according to the present teachings shown with two retractor blades.
Figure 6:
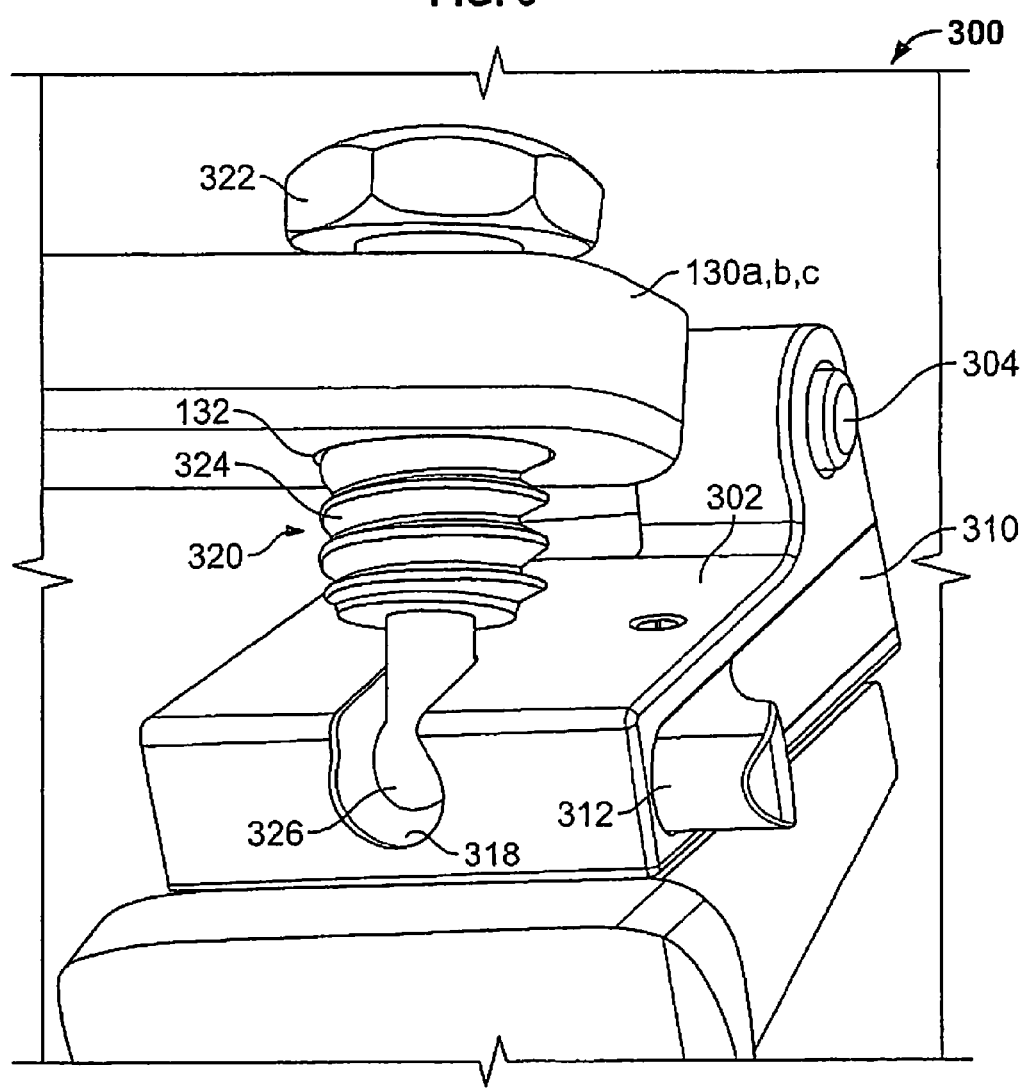
FIG. 6 is an enlarged view of Detail B of FIG. 4.
Figure 8:
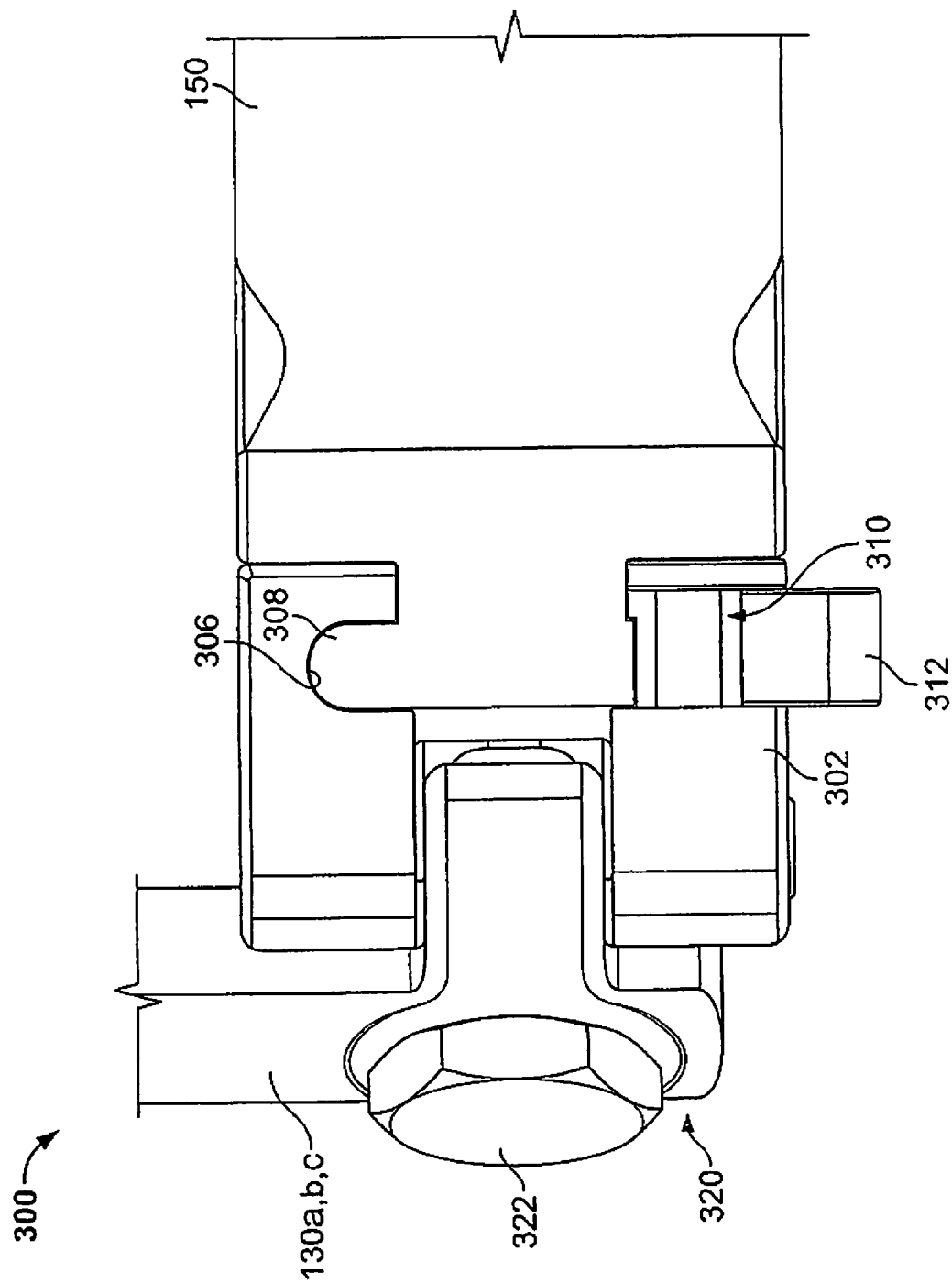
FIG. 8 is an enlarged sectional view of Detail C of FIG. 4.

The distal end of each of the first and second retractor arms 130a, 130b (generically referenced as 130) can be coupled to a blade angulator/connector 300, as illustrated in FIGS. 4, 6 and 8, for connecting a blade 150 to the retractor arm 130 in a quick-connect, self-locking manner. The blade angulator/connector 300 can include a blade holder 302 pivotably connected to the retractor arm 130 with a pivot element 304. The blade holder 302 can include a male or female quick-engagement formation 306 couplable with a conforming female or male quick-engagement formation 308 on the blade 150. The quick engagement formations 306, 308 can define a dovetail-type tongue-and-groove connection, for example, a pocket connection or other type of quick-connect/disconnect arrangement. The blade connector 300 can include a locking arm 310 biased to lock the blade 150 in the blade holder 302 in a self-locking manner. Pressing extension 312 of the locking arm 310 rotates the locking arm 310 to a release position that allows the blade 150 to be removed.

The blade connector 300 can also include a driver 320 that can control the rotation of the blade holder 302 and thereby the angulation or tilting of the blade 150 relative to the retractor arm 130. The driver 320 can include a head 322, a threaded portion 324 and a distal end 326. The driver 320 can be threaded through a threaded bore 132 of the retractor arm 130 such that the distal end 326 can engage a slot or groove or other channel 318 defined in the blade holder 302. The distal end 326 can be shaped to be rotatably and slidably received in the channel 318. The distal end 326 can have, for example a spherical or other bulbous shape. The driver 320 can be designed such that the driver 320 cannot be completely disengaged from the blade holder 302 during the full range of motion of the driver 320. Rotating the head 322 pivots the blade holder 302 and the attached blade 150 relative to the retractor arm 130, as shown in FIG. 7. Accordingly, the degree of angulation or tilting of the blade 150 can be continuously controlled and adjusted.

Figure 9A:
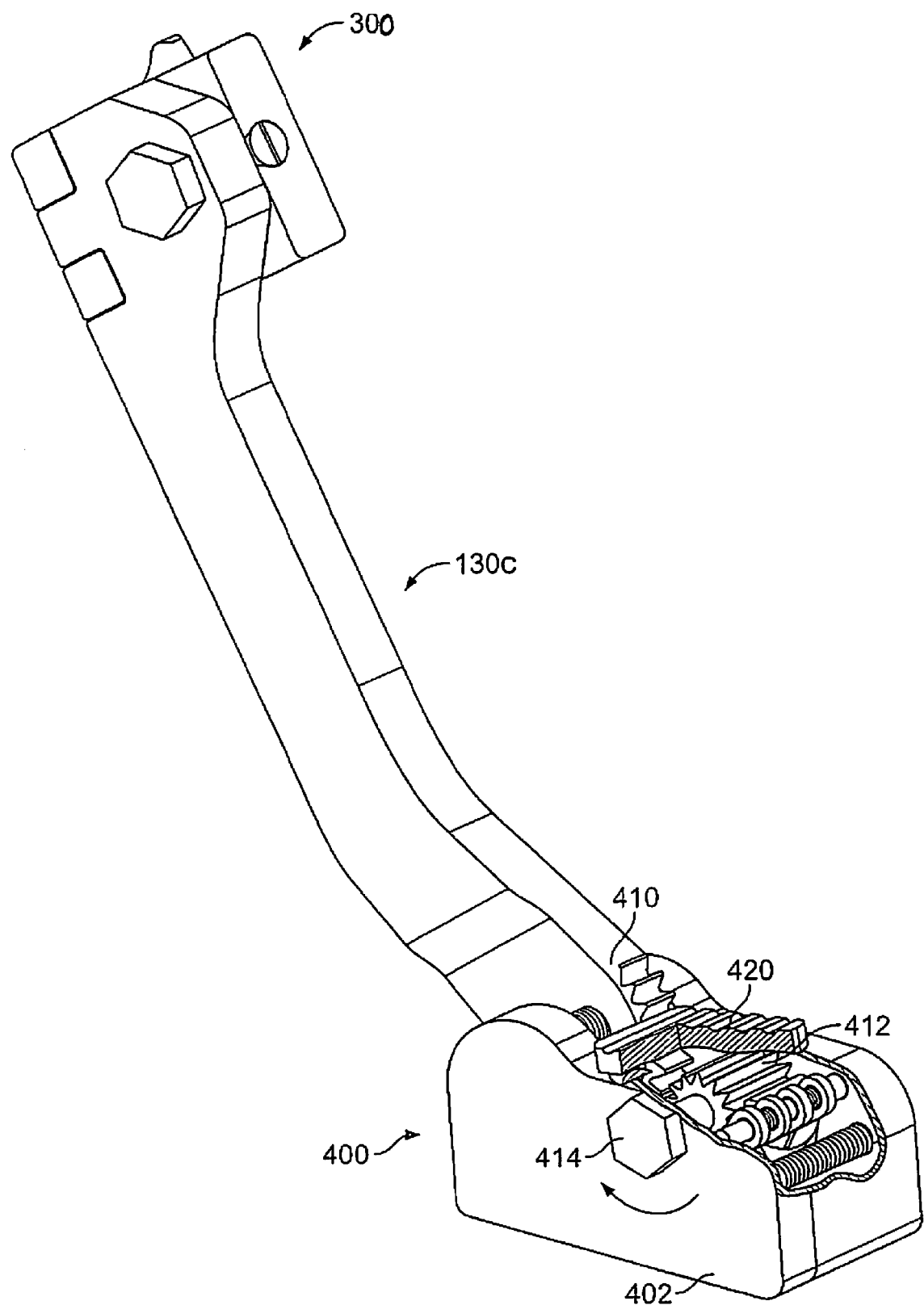
FIGS. 9A and 9B are perspective views of an exemplary retractor arm according to the present teachings, the modular arm shown with a partial cut-away view of one end.
Figure 9B:
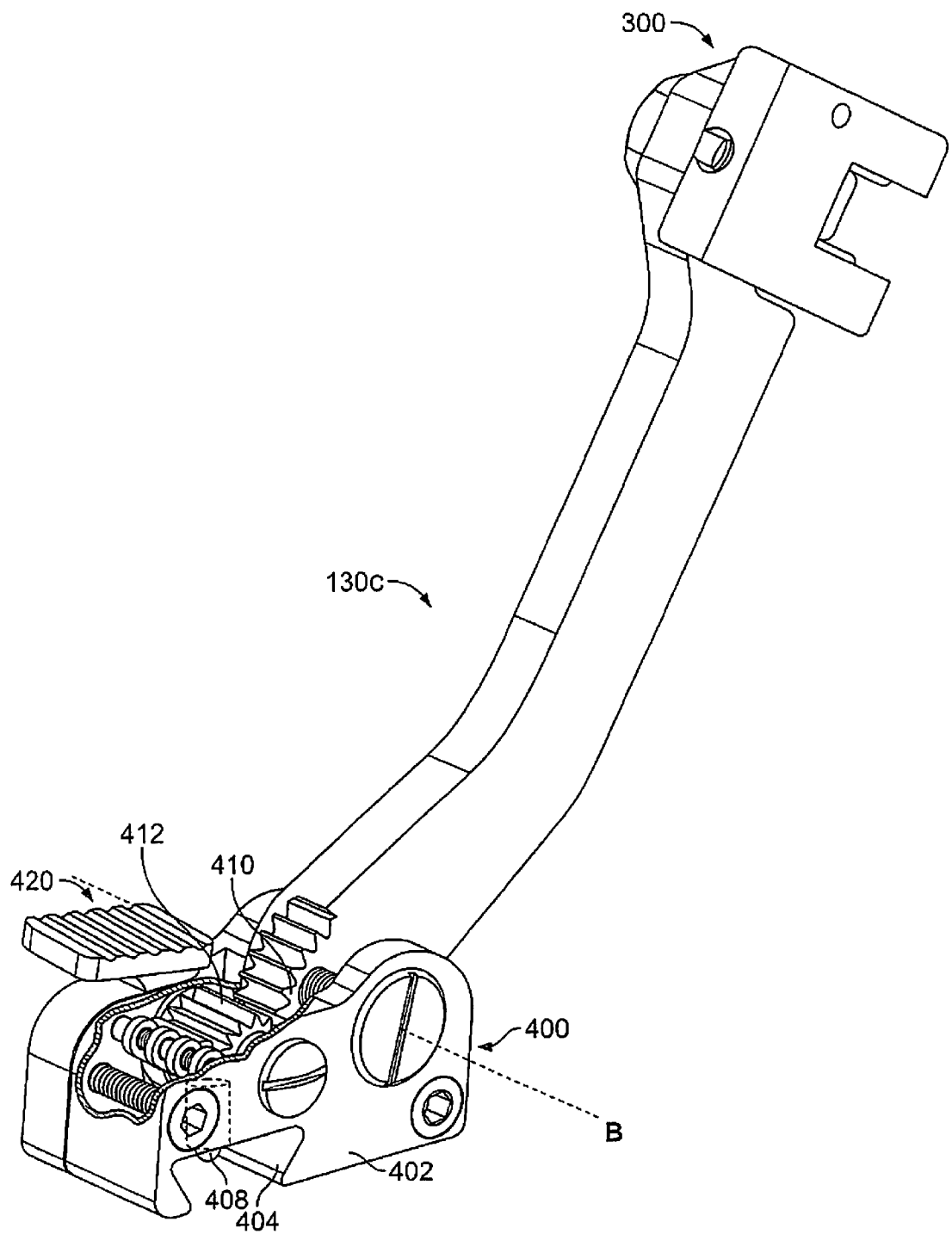

Referring to FIGS. 1, 9A and 9B, additional distraction can be provided as desired by connecting to the frame 101 multiple modular arms 130c. The modular arms 130c can be connected to the inner frame member 104 using a quick connect/disconnect arm connector 400. A blade connector, such as the blade connector 300 described above, can be used to connect the modular arm 130c to a blade 150 self-lockingly and with continuous adjustment control. The blade connector 300 can provide angulation that is independent for each blade 150 connected to the frame 101.

The arm connector 400 can allow each modular arm 130c to distract independently of any other modular arm 130c or retractor arm 130, 130a, 130b and can provide a self-locking and quick release connection. The arm connector 400 can include a modular housing 402 defining a quick-engagement formation 404 which can be engaged to a corresponding quick-engagement formation 406 on the frame 101 as shown in FIG. 7. The quick-engagement formations 404, 406 can be of the dovetail, pocket or quick-connect engagement type and can be self-locking. The exemplary arm connector 400 is shown, for example, with female/male dovetail formations 404, 406. A spring-loaded ball plunger 408 can be supported by the housing 402 to provide self-locking for the engagement formations 404, 406.

The modular arm 130c can include a gear 410 coupled to the housing 402 and engageable with a pinion 412 supported by the housing 402. A hex head or other actuating element 414 can be connected to the shaft of the pinion 412 to rotate the pinion. The pinion 412 can transfer rotational motion to the gear 410 and rotate the modular arm 130c about pivot axis B. Axis B is generally perpendicular to the frame pivot axis A. A trigger 420 can be activated to release a trigger lock that prevents rotational motion.

The retractor device 100 can be used with various arm combinations coupled to the frame 101. For example, FIG. 1 illustrates the frame 101 assembled with four blades 150. It will be appreciated that a smaller number of blades 150 or even a single blade 150 can be used with the frame 101. Similarly, more than four blades 150 can be used, if desired. The blades 150 can be curved or flat and can be of different widths, diameters, and lengths. Some blades 150 can define a blade channel that can be used to introduce a light source or a blade extension or a utility tool, such as a suction pump or other device.

The various components of the retractor device 100, including the outer and inner frame members 102, 104, the retractor arms 130a, 130b, the modular arms 130c, and the blades 150, can be made of metallic or polymeric materials. Polymer materials with radiolucent properties may be used when increased visibility is desirable.

The various control devices, including the frame driver 200, the distraction driver 250, the blade angulator/connector 300, and the arm connector 400, can be adjusted using a wrench, a detachable knob or other tool. The modular arms 130c can also be manually moved in the permissible rotational directions.

Turning now to FIGS. 10A-14B, various additional retractor blades 500 in accordance with the present teachings are illustrated and will now be described. In view of the common features between the various retractor blades 500, common reference numerals will be used to identify similar features throughout. The retractor blades 500 are particularly adapted for use with a surgical retractor device such as the surgical retractor device 100 described above. It will be appreciated, however, that the present teachings are not so limited and may be readily adapted for alternate applications.

The retractor blades 500 of the present teachings may generally include a base portion 502 and a distal portion or tip 504. The distal portion 504 may be removably attached to the base portion 502. In this fashion, the distal portion 504 may be a single-use, disposable component.

The base and distal portions 502 and 504 of the blade 500 may be constructed of distinct materials. In one application, the base portion 502 may be constructed of a metal or other suitable material having sufficient strength and durability characteristics. The material of the base portion 502 may be suitable for surgical sterilization. The distal portion 504 may be constructed of plastic or other suitable material. The distal portion 504 may be a single-use, disposable component.

The base portion 502 may be curved, flat or of any other suitable geometry. The base portion 502 may be of any suitable width, diameter, and length. Exemplary base portions 502 are shown throughout the drawings. The base portion 502 may include a keyed featured 606 to interface with an instrument. A quick connect feature 505 may be provided to quickly couple the surgical retractor blade 500 to a frame for distraction. In certain embodiments, the blade base may include a clip or hook feature 507 (see FIG. 11C) to guide a light source, such as a light cable, as shown, for example, in FIGS. 14A and 14B.

The distal portion 504 may be curved, flat or of any other suitable geometry. In general, the geometry of the distal portion 504 may complement the geometry of the base portion 502. Similar to the base portion 502, the distal portion 504 may be of any suitable width, diameter, and length. Exemplary distal portions 504 are shown throughout the drawings.

Figure 10C:
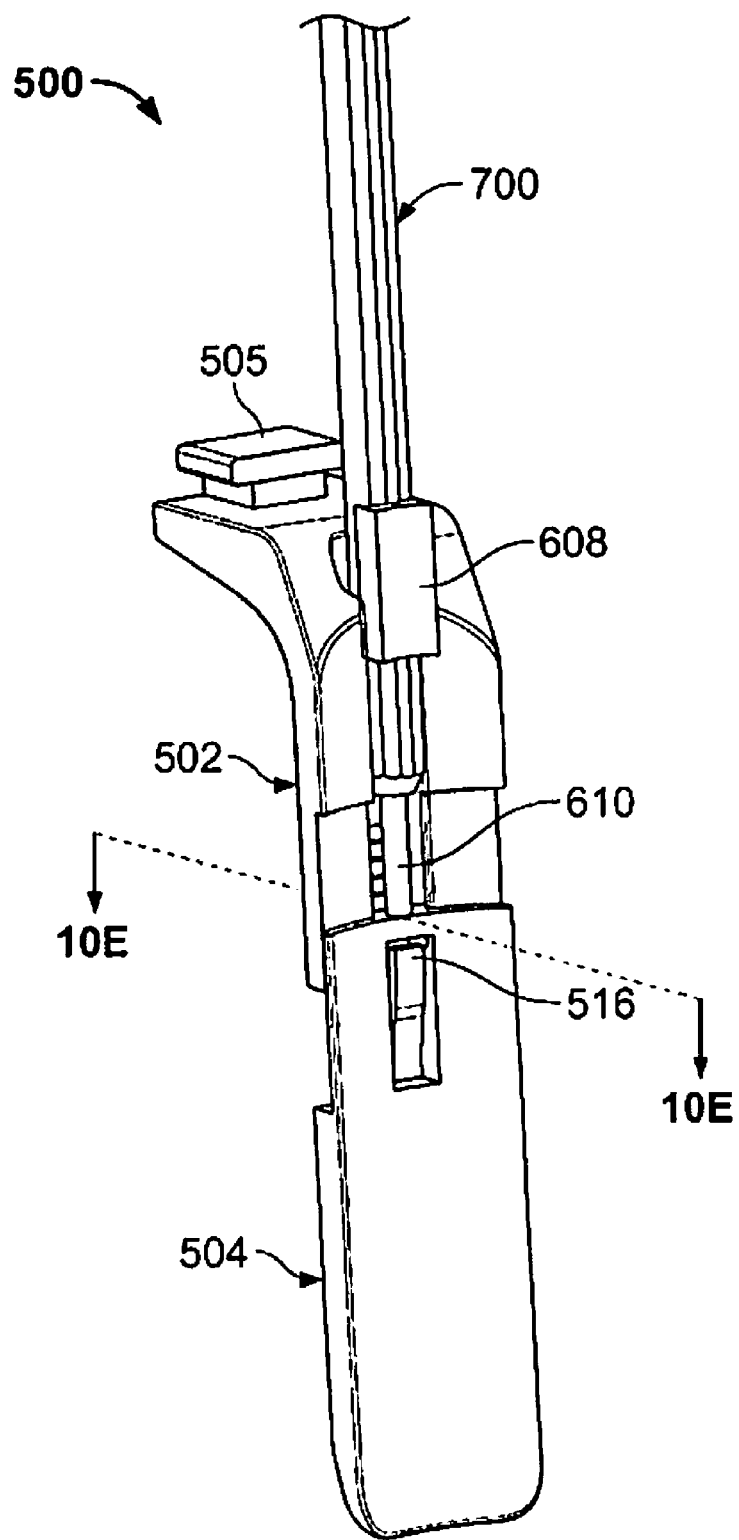
Figure 10D:
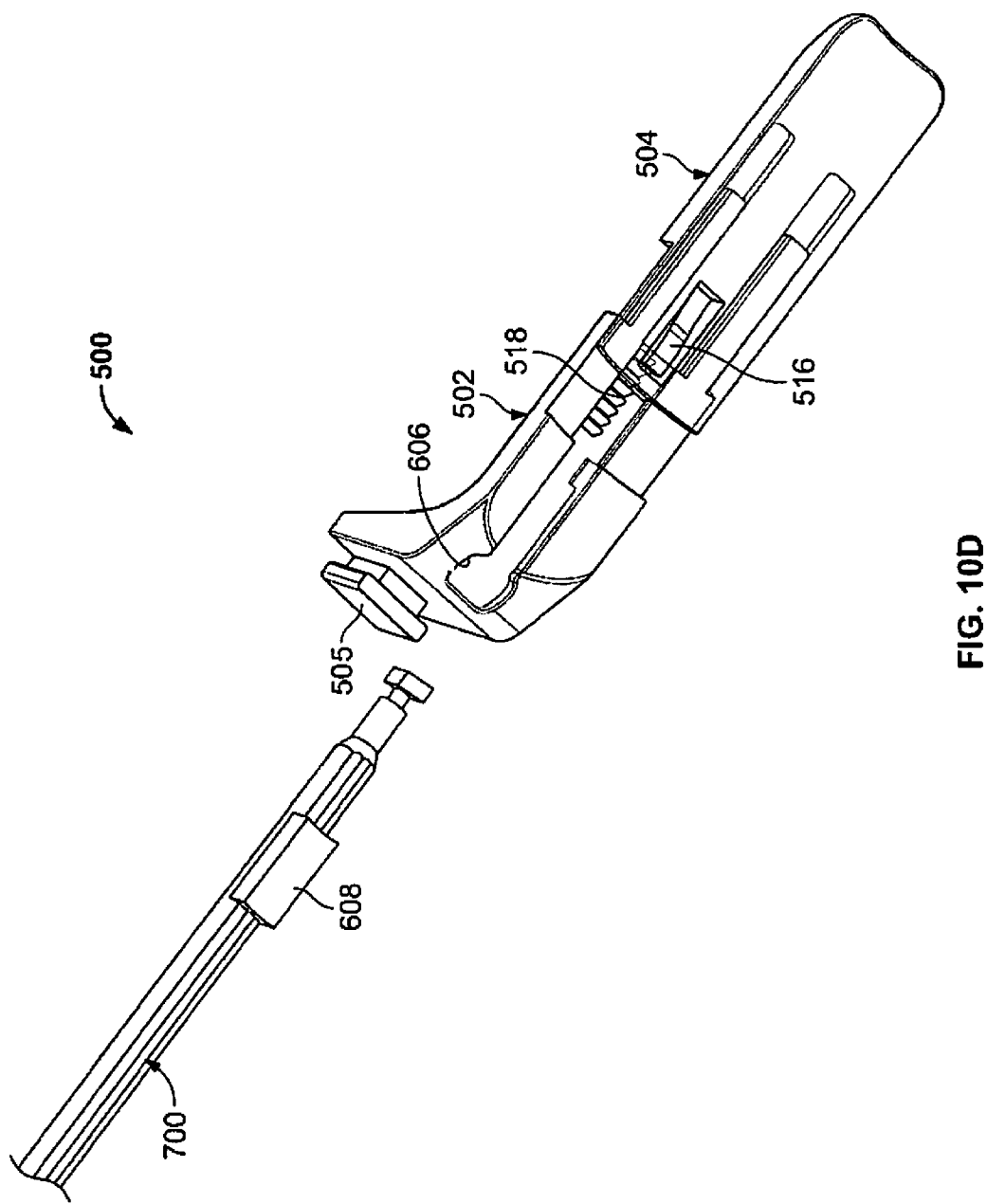
Figure 10E:
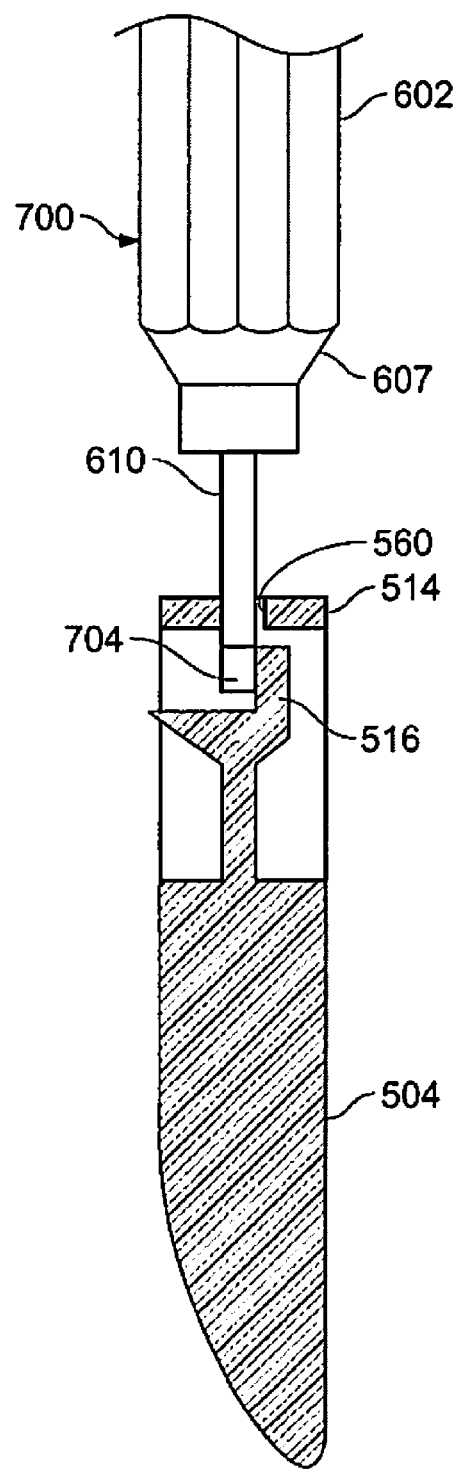
FIGS. 10E and 10F are sectional views taken along the line 10E-10F of FIG. 10C.
Figure 10F:
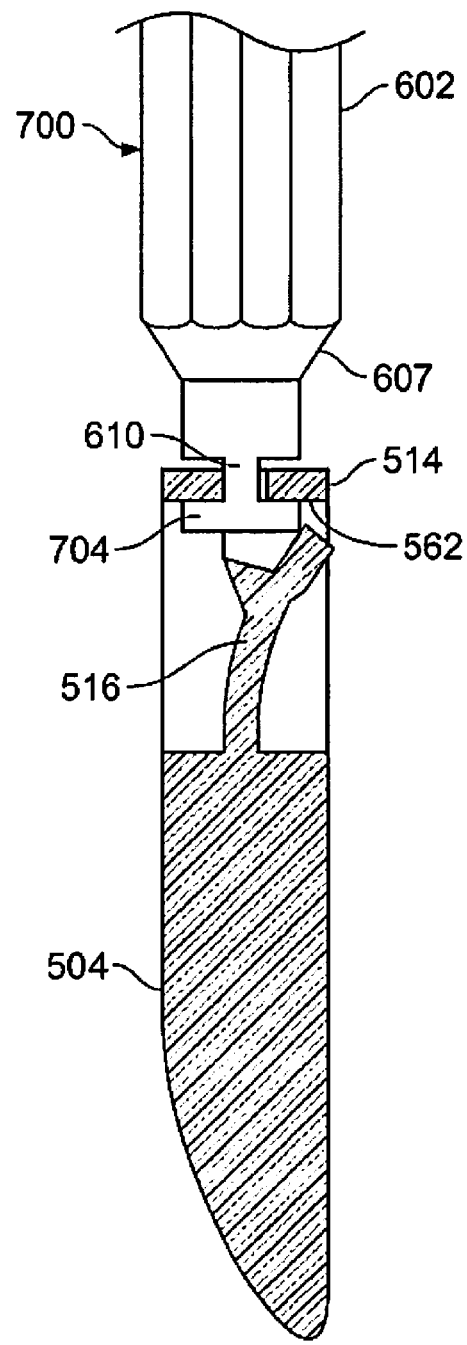
Figure 11A:
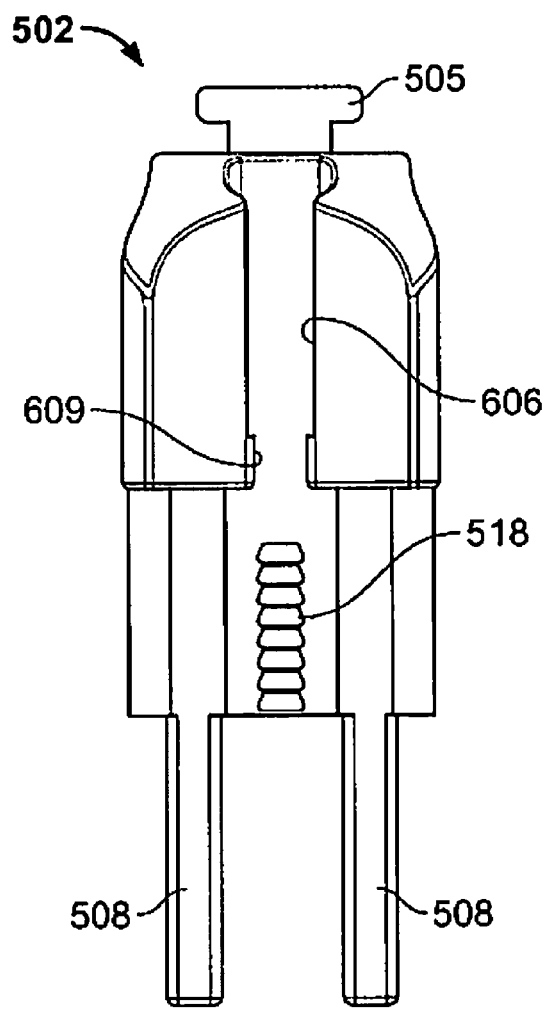
FIG. 11A is a front view of a base portion of a blade assembly according to the present teachings.
Figure 11B:
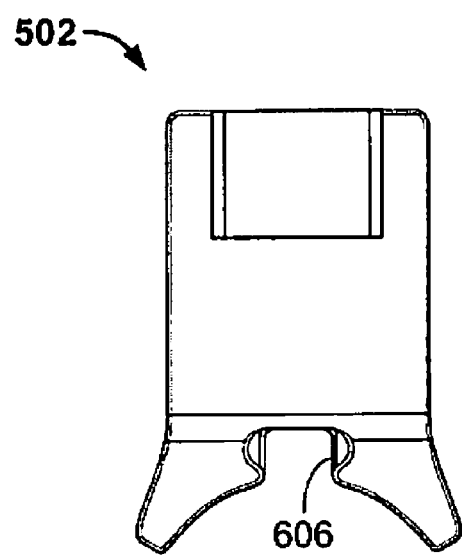
FIG. 11B is a top view of the base portion of FIG. 11A.
Figure 11C:
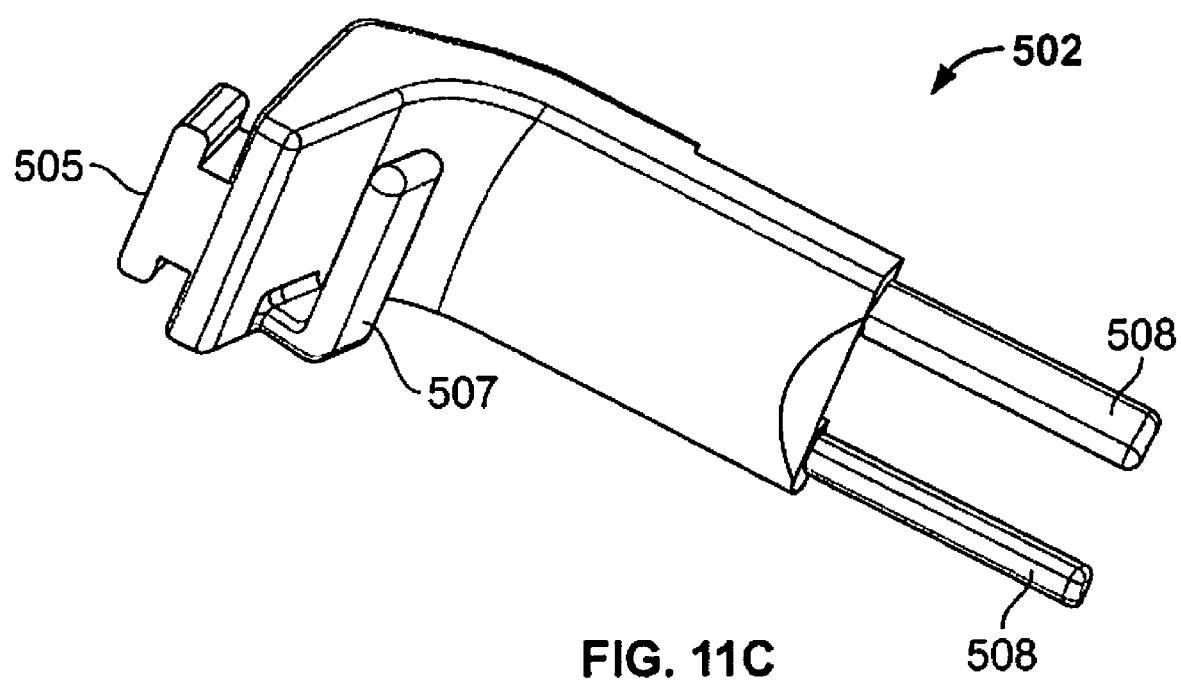
FIG. 11C is a rear perspective view of the base portion of FIG. 11A.
Figure 12A:
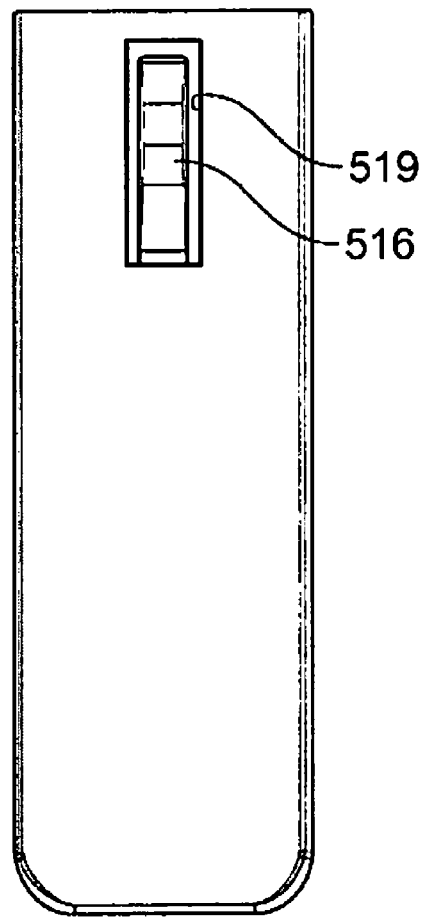
FIG. 12A is a front view of a distal portion of a blade assembly in accordance with the present teachings.
Figure 12B:
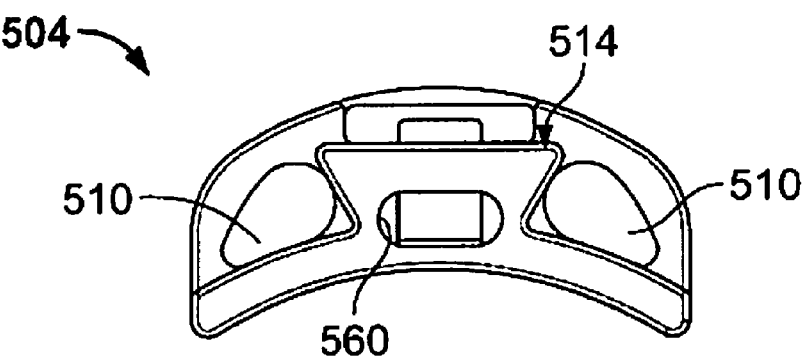
FIG. 12B is a top view of the distal portion of FIG. 12A.
Figure 13A:
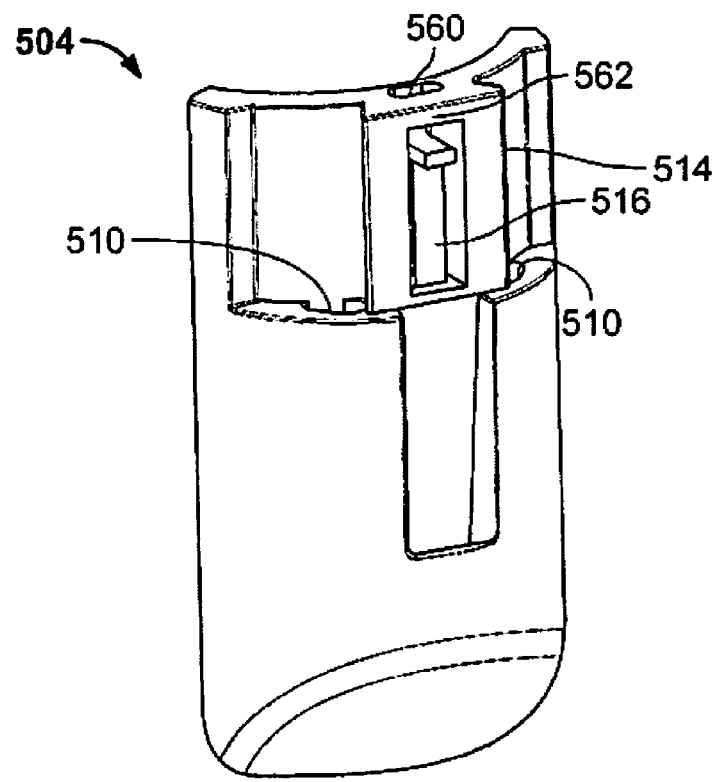
FIGS. 13A and 13B are rear perspective views of additional distal portions for blade assemblies in accordance with the present teachings.
Figure 13B:
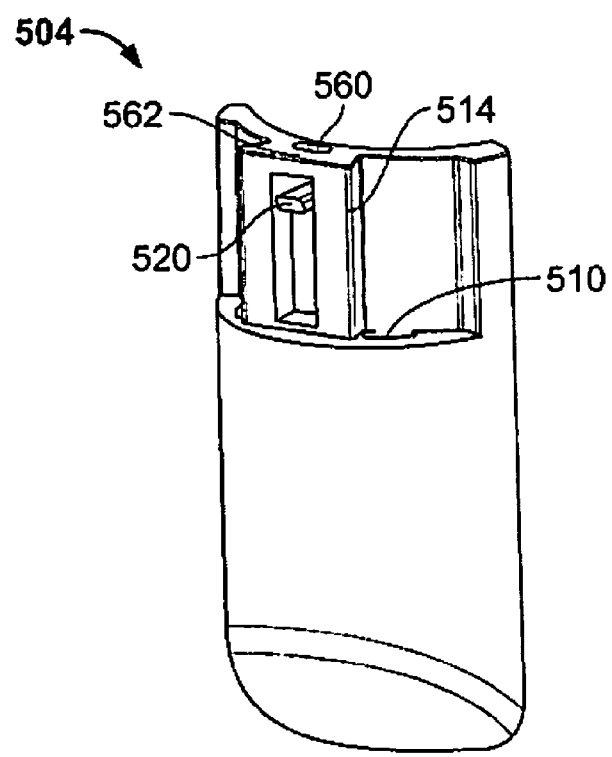

As particularly shown in FIGS. 10A-10B, the distal portion 504 may be coupled to the base portion 502 in a manner that allows relative movement therebetween. The distal portion 504 may be translated between a first position or fully retracted position (shown in FIG. 10A) and a second position or fully extended position (shown in FIG. 10D). Intermediate positions are shown in FIGS. 10B and 10C. As will be further discussed below, the distal portion 504 may be positively located relative to the base portion 502 in at least these plurality of positions.

The base and distal portions 502 and 504 may be cooperatively configured to facilitate movement of the distal portion 504 from the first position to the second position. As shown in the drawings, the base portion 502 may include a pair of outwardly extending legs 508 received in corresponding channels 510 defined by the distal portion 504. The legs 508 may both have a generally teardrop shape corresponding to the shape of the channels 510 as particularly shown in FIG. 12B. An upper portion of the distal portion 504 may carry an extension 514 positioned between and above the upper ends of the channels 510. The legs 508 may straddle the extension 514 in a dovetail-type relationship which may add stability to the blade 500 while the distal portion or tip 504 is extended. The extension 514 may be located along a longitudinal centerline of the distal portion 504.

As particularly shown in FIGS. 10A-10C, the distal portion 504 may be held at multiple positions of extension relative to the base portion 502 to prevent tissue creep under the distal portion 504. As will be discussed further below, the base and distal portions 502 and 504 may cooperate to allow downward translation of the distal portion 504 and normally oppose upward translation of the distal portion 504. Extension of the distal portion 504 may be maintained through a ratchet-type arrangement or similar structure.

The ratchet-type arrangement may include a spring tab 516 carried by one of the base portion 502 and distal portion 504 and a plurality of retention features 518 carried by the other of the base portion 502 and distal portion 504. As shown in the drawings, the spring tab 516 is carried by and integrally formed with the distal portion 504. The plurality of retention features 518 are carried by and integrally formed with the base portion 502. The retention features may be a plurality of grooves 518 extending into the base portion 502 or a plurality of ridges or teeth extending from the base portion 502.

The spring tab 516 may be located within a window 519 (see FIG. 12A, for example) defined by the base portion 502. The spring tab 516 may include an upper end 520 (see FIG. 13B, for example) extending toward the plurality of retention features 519. The upper end 520 may normally engage the retention features 519 and may be resiliently deflected away from the retention features 519. The upper end 520 may include a tapered face which angles away from the retention features 519 as it extends downward such that the retention features 519 will not prevent downward translation of the distal portion 504 but will oppose upward translation.

Figure 14A:
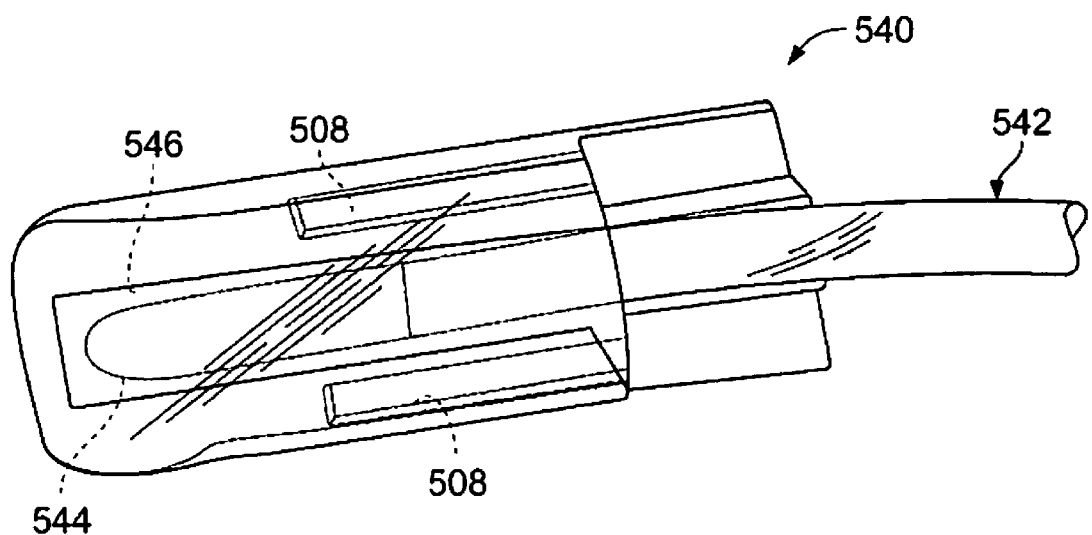
FIGS. 14A and 14B are perspective views of a distal portion of a blade assembly in accordance with the present teachings shown operatively associated with a light source.
Figure 14B:
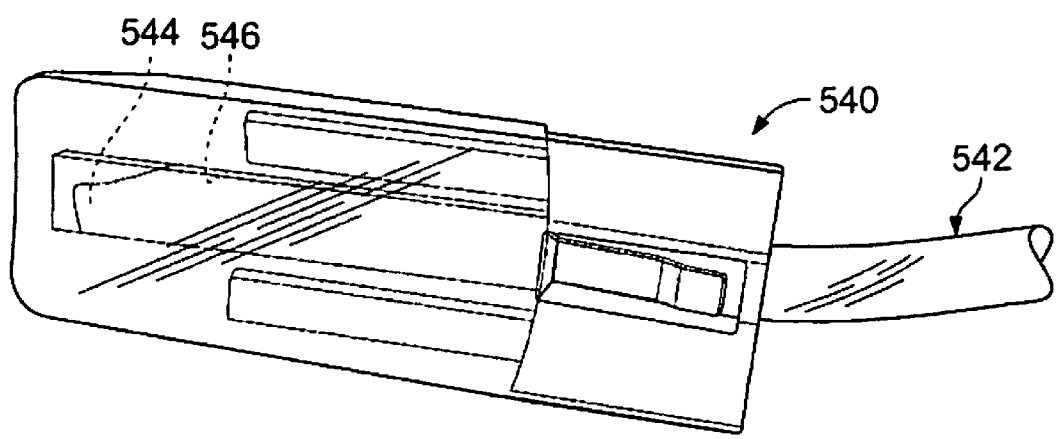

Referring to FIGS. 14A and 14B, another distal portion 540 in accordance with the present teachings is illustrated. The distal portion 540 may be constructed of a translucent material. One particular material is a polycarbonate commercially available under the tradename Lexan 104. Alternatively, the distal portion 540 may be constructed of one or more other suitable materials. To the extent not otherwise described, the distal portion 540 will be understood to be substantially identical to the distal portions 504 described above.

The distal portion 540 is shown operatively associated with a light source 542. The light source 542 may be fiber optic or an LED light source. The light source 542 may be affixed to the distal portion 540 in any well known manner. As illustrated in the drawings, an end 544 of the light source 542 may extend into a pocket 546 defined by the distal portion 540. In certain applications, the light source 542 may be permanently affixed to the pocket 546. Alternatively, the light source 542 may be removably attached to the distal portion 540. In this manner, the distal portion 540 may transmit light for illuminating a surgical opening.

Figure 16:
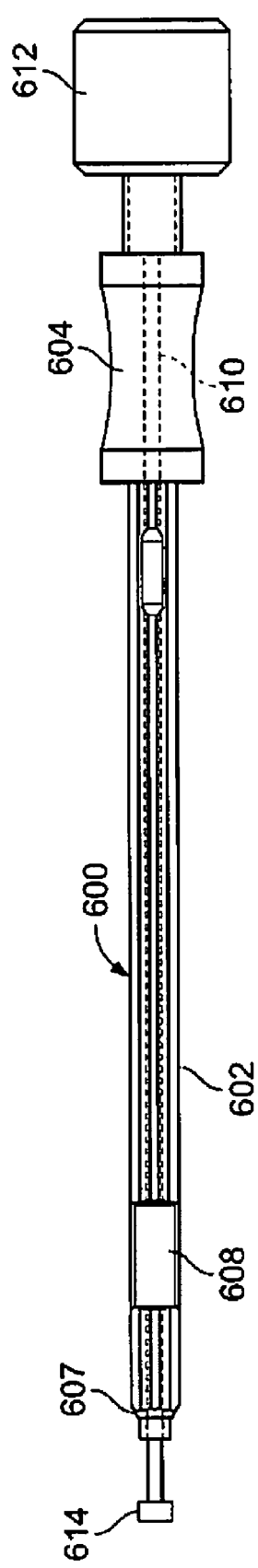
FIG. 16 is a side view of the extension instrument shown in FIG. 10C.
Figure 17:
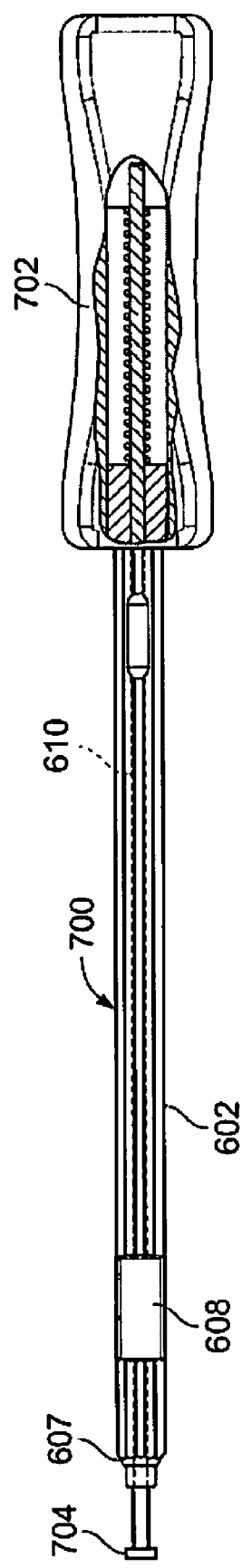
FIG. 17 is a side view of the retraction instrument shown partially in FIG. 10D, the instrument shown partially cut-away.

One particular blade extension instrument 600 is shown operatively associated with one of the blades in FIG. 10B and further shown in FIG. 16. One particular blade retraction instrument 700 is operatively shown with one of the blades 500 in FIGS. 10C and 10D and in further detail in FIG. 17.

The blade extension instrument 600 may include a hollow shaft 602 and a handle 604. The hollow shaft 602 may be sized to be received within a channel 606 defined by the base portion 502. A stabilization element 608 may be carried by the shaft 602 and sized and positioned to cooperate with the channel 606 to prevent rotation of the shaft 602. The shaft 602 may include a reduced diameter distal end 607 that is matingly received in a reduced diameter lower portion 609 of the channel 606.

The blade extension instrument 600 may further include a rod 610 passing through the hollow shaft 602. At a proximal end, the rod 610 may be coupled to a knob 612 or other control element. The rod 610 is threadably coupled within the instrument 600 such that rotation of the knob 612 in a first direction (e.g., clockwise) advances the rod 610 and rotation of the knob in a second direction (e.g., counterclockwise) retracts the rod 610. At a distal end, the rod 610 may be connected to an enlarged tip 614.

In operation, the knob 612 may be rotated to advance the rod 610 and thereby downwardly translate the tip 614. The tip 614 opposes the extension 514 of the distal portion 504. Translation of the rod 610 overcomes friction forces and moves the distal portion 504 toward the fully extended position. Travel of the distal tip 614 may be limited (e.g., to approximately 10 mm or other value) to prevent over-extension of the distal portion 504.

The blade retraction instrument 700 may disengage the spring tab 516 from the retention features 519 to allow blade retraction. As with the extension instrument 600, the retraction instrument used for blade retraction 700 may be shaped to interface with the channel 606 on the base portion 502 to prevent disengagement. Common shaft features are identified with common reference numbers.

The blade retraction instrument 700 may similarly include a rod 610 passing through the hollow shaft 602. At a proximal end, the rod 610 may be connected to a rotatable handle. At a distal end, the rod 610 may be coupled to a T-shaped tip 704. The rod 610 is coupled within the instrument 700 such that rotation of the handle 702 rotates the rod 610 and tip 704.

The blade retraction instrument 700 may similarly include a common hollow shaft 602. The hollow shaft 602 is able to rotate independently of the handle 702 and shaft 610. The hollow shaft 602 is forced downward towards the tip 704 by a spring in the handle 702. The downward force aids in assembly by retracting the distal portion 504 onto the base portion 502.

In operation, the shaft 602 of the instrument 700 is placed within the channel 606. The rod 610 is extended and the tip 704 is advanced into an opening 560 in an upper end of the extension 514. Rotation of the tip 704 through approximately ninety degrees prevents removal of the tip 704 from the opening 560 through engagement with a surface 562. Such rotation also causes engagement of the tip 704 with an inwardly extending flange 566 (see FIG. 12A) carried by an upper end of the spring tab 516. This engagement outwardly displaces the spring tab 516 in the direction of arrow A (see FIG. 12B) against the inherent bias of the spring tab 516.

Figure 15A:
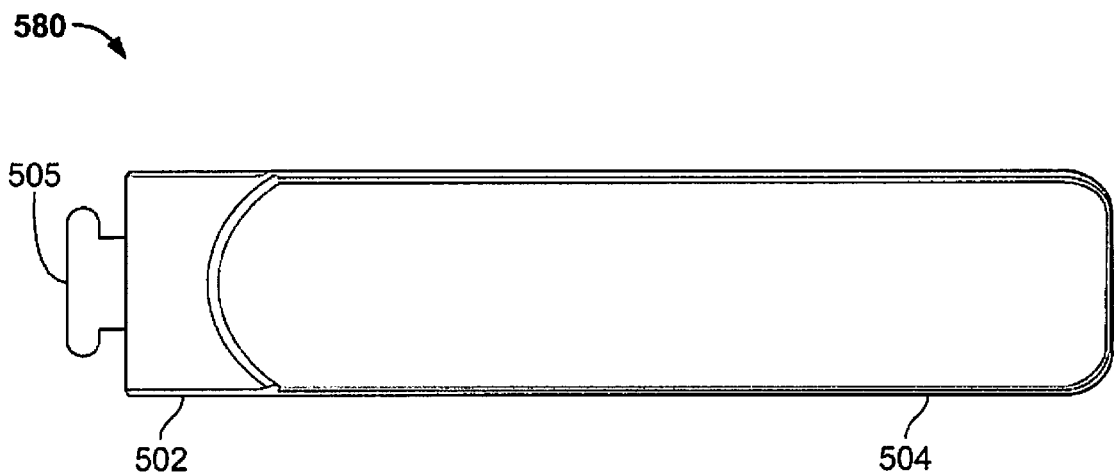
FIG. 15A is a front view of another retractor blade in accordance with the present teachings.
Figure 15B:
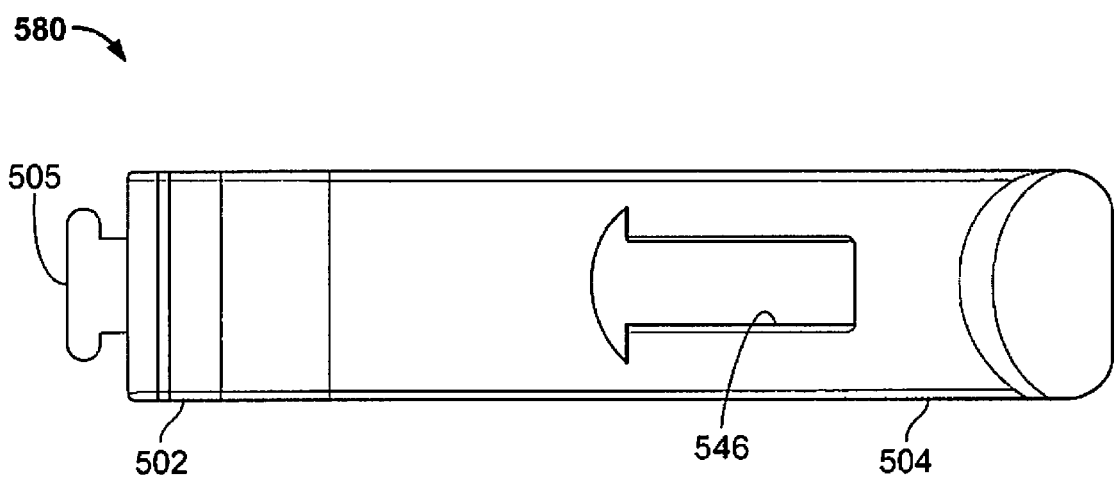
FIG. 15B is a rear view of another retractor blade in accordance with the present teachings.

With reference to FIGS. 15A and 15B, another surgical retractor blade 580 according to the present teachings is illustrated. As illustrated, the surgical retractor blade 580 is constructed as a single component. The single component may fulfill the functionality of both the base portion 502 and distal portion 504. In this regard, the single component may include a base portion 502 and a distal portion 504. These two portions 502 and 504 may be constructed of a common material or multiple materials (molded plastic parts with steel inserts). This single component could be a plurality of lengths, widths, and diameters. The surgical retractor blade 580 may include a pocket 546 for lighting. The surgical retractor blade 580 may be a surgical retractor blade. In this regard, the surgical retractor blade 580 may be a single-use, disposable component.

The foregoing discussion discloses and describes merely exemplary arrangements of the present invention. One skilled in the art will readily recognize from such discussion, and from the accompanying drawings and claims, that various changes, modifications and variations can be made therein without departing from the spirit and scope of the invention as defined in the following claims.

What is claimed is:

1. A blade for a surgical retractor, the blade comprising:
   a base portion for attaching to a frame, the base portion constructed of a first material and defining a first discrete leg and second discrete leg that each extend along an axis parallel to a longitudinal axis of the blade; and
   a distal portion defining a pair of channels that each extend along an axis parallel to the longitudinal axis of the blade and cooperate with each of the first leg and the second leg of the base portion to enable the distal portion to translate relative to the base portion in only one direction, the distal portion constructed of a second material, the second material being different than the first material,
   wherein the distal portion includes an extension formed between the pair of channels such that the extension and the pair of legs cooperate to form a dovetail relationship.

2. The blade of claim 1, wherein the distal portion is unitarily constructed of a plastic material.

3. The blade of claim 1, wherein the distal portion is unitarily constructed of a translucent material.

4. The blade of claim 3, wherein the distal portion is mounted to the base portion so as to extend beyond the base portion.

5. The blade of claim 1, wherein the distal portion is constructed of a disposable material.

6. The blade of claim 1, wherein the base portion includes a keyed channel for receiving an instrument to engage a spring tab on the distal portion.

7. The blade of claim 6, wherein the instrument comprises a blade extension instrument having a tip that engages the spring tab to move the distal portion from a first, retracted position to a second, extended position.

8. The blade of claim 6, wherein the instrument comprises a blade retraction instrument having a T-shaped tip that engages the spring tab to move the distal portion from a second, extended position to a first, retracted position.

9. A blade for a surgical retractor, the blade comprising:
   a base portion for attaching to a frame, the base portion defining a pair of legs;
   a distal portion defining a pair of channels that each extend along an axis parallel to a longitudinal axis of the blade and having an extension formed between the pair of channels, the pair of channels slidably receiving the pair of legs, the distal portion removably coupled to the base portion, the distal portion unitarily constructed of a translucent material;
   a ratchet mechanism for adjustably coupling the distal portion with the base portion; and
   a light source removably coupled to the distal portion,
   wherein the pair of legs and the extension cooperate to form a dovetail relationship that provides stability during the movement of the distal portion relative to the base portion.

10. The blade of claim 9, wherein the distal portion is constructed of a disposable material.

11. The blade of claim 9, wherein the light source is a fiber optic cable light source or LED.

12. The blade of claim 11, further comprising a clip to guide the fiber optic cable along the base portion.

13. The blade of claim 9, wherein the base portion includes a keyed channel for receiving an instrument to engage with the distal portion.

14. The blade of claim 9, wherein each of the first leg and the second leg has a generally teardrop shape.

15. The blade of claim 9, wherein the light source is removably received within a pocket formed in the distal portion.

16. A method of retracting a surgical opening comprising:
   providing a frame and a retractor blade having a base portion secured to the frame, the base portion defining a first discrete leg and a second discrete leg;
   removably attaching a translucent distal portion to the base portion by slidably receiving each of the first leg and the second leg within a pair of channels extending along an axis parallel to a longitudinal axis of the distal portion;
   adjusting the distal portion relative to the base portion and securing the distal and base portions with a ratchet mechanism;
   positioning a light source within a pocket defined in the translucent distal portion;
   retracting the surgical opening with the distal portion;
   illuminating the surgical opening with a light source secured to the translucent distal portion; and
   disposing of the distal portion.

* * * * *

UNITED STATES PATENT AND TRADEMARK OFFICE
CERTIFICATE OF CORRECTION

| | | |
|---|---|---|
| PATENT NO. | : 7,922,658 B2 | Page 1 of 1 |
| APPLICATION NO. | : 12/256106 | |
| DATED | : April 12, 2011 | |
| INVENTOR(S) | : Dan S. Cohen et al. | |

It is certified that error appears in the above-identified patent and that said Letters Patent is hereby corrected as shown below:

Column 1, line 13, insert -- INTRODUCTION --

Column 2, line 13, "and distraction" should be -- a distraction --

Column 2, line 27, "end." should be -- end; --

Column 4, line 11, "by a moving" should be -- by moving --

Signed and Sealed this
Seventeenth Day of July, 2012

David J. Kappos
*Director of the United States Patent and Trademark Office*